US010887735B2

(12) United States Patent
Castonzo (10) Patent No.: US 10,887,735 B2
(45) Date of Patent: Jan. 5, 2021

(54) VACCINE MONITORING SYSTEM (71) Applicant: Kiwanis International, Inc., Indianapolis, IN (US)

(72) Inventor: Thomas Castonzo, Fort Wayne, IN (US)

(73) Assignee: Kiwanis International, Inc., Indianapolis, IN (US)

( * ) Notice: Subject to any disclaimer, the term of this patent is extended or adjusted under 35 U.S.C. 154(b) by 0 days.

(21) Appl. No.: 16/418,518

(22) Filed: May 21, 2019

(65) Prior Publication Data
US 2019/0364398 A1 Nov. 28, 2019

Related U.S. Application Data (60) Provisional application No. 62/676,064, filed on May 24, 2018.

(51) Int. Cl.
| G08C 19/12 | (2006.01) |
| G08C 19/16 | (2006.01) |
| H04W 4/38 | (2018.01) |
| H04Q 9/00 | (2006.01) |
| H04W 4/029 | (2018.01) |
| G08B 21/18 | (2006.01) |
| A61J 1/16 | (2006.01) |
| A61K 39/08 | (2006.01) |

(52) U.S. Cl.
CPC .............. *H04W 4/38* (2018.02); *A61J 1/16* (2013.01); *G08B 21/182* (2013.01); *H04Q 9/00* (2013.01); *H04W 4/029* (2018.02); *A61J 2200/50* (2013.01); *A61J 2200/72* (2013.01); *A61K 39/08* (2013.01); *H04Q 2209/40* (2013.01); *H04Q 2209/823* (2013.01)

(58) Field of Classification Search
CPC .. H04W 4/38; H04W 4/029; A61J 1/16; A61J 2200/50; A61J 2200/72; A61J 1/165; A61J 2200/70; G08B 21/182; H04Q 9/00; H04Q 2209/823; H04Q 2209/40; A61K 39/08; G16H 10/00
USPC .................................................... 340/870.17
See application file for complete search history.

(56) References Cited

U.S. PATENT DOCUMENTS

| 2017/0200212 A1* | 7/2017 | Garrity ................. G06F 16/955 |
| 2018/0003572 A1* | 1/2018 | Garsd ..................... G01K 13/00 |
| 2018/0270843 A1* | 9/2018 | Jiang ................ H04W 52/0216 |

OTHER PUBLICATIONS

CAS Dataloggers, Chesterland OH, The 6 most important parts of a temperature monitoring system, Jun. 25, 2014, 1-12 (Year: 2014).*

(Continued)

*Primary Examiner* — Tanmay K Shah
(74) *Attorney, Agent, or Firm* — Taft Stettinius & Hollister LLP (57) ABSTRACT A method according to one embodiment includes receiving, by a control system secured to the insulated portable container, sensor data from a temperature sensor positioned within the insulated portable container, determining, by the control system, whether the sensor data is associated with a notification range, establishing, by the control system, a long-range wireless communication connection with a server in response to a determination that the sensor data is associated with the notification range, and transmitting, by the control system, a message to the server indicating that the sensor data is associated with the notification range in response to establishing the long-range wireless communication connection.

20 Claims, 7 Drawing Sheets

(56) References Cited

OTHER PUBLICATIONS

Vaccine Storage and Handling Toolkit, CDC, Jan. 2019 (Year: 2019).*

* cited by examiner

VACCINE MONITORING SYSTEM

CROSS-REFERENCE TO RELATED APPLICATIONS

This application claims the benefit of U.S. Provisional Application No. 62/676,064 filed on May 24, 2018, the contents of which are incorporated herein by reference in their entirety.

BACKGROUND

Humanitarian organizations have been engaged in campaigns directed to the worldwide and/or regional elimination of neonatal and maternal tetanus and performing other routine immunization. In doing so, tetanus-containing and other vaccines are often transported to villages in low-income and middle-income countries, geopolitically hostile territories, and remote regions of the world using even the most rudimentary types of transportation. For example, vaccines are often transported in simple insulated coolers and carried by animal or manually by human. Unfortunately, the efficacy of the vaccines may be diminished completely if the temperature of the vaccines surpasses specific temperature limits, and typically neither the vaccination field team transporting the vaccines nor the sponsoring organization is aware of the expiration until arrival of the team at the target destination (i.e., when finally opening the cooler).

SUMMARY

According to an embodiment, a vaccine monitoring system may include a server comprising a first processor and a first memory having a first plurality of instructions stored thereon and an insulated portable container for transporting a tetanus-containing vaccine in a temperature-stable environment. The insulated portable container may be structured to be less than four cubic feet in size and may include a housing having a first chamber defined therein that stores the tetanus-containing vaccine during transport of the tetanus-containing vaccine, a buffered temperature sensor container defining a second chamber that houses a buffering agent, a temperature sensor positioned within the buffering agent that generates sensor data representative of a temperature of the tetanus-containing vaccine, and a microcontroller secured to the housing within the first chamber, electrically coupled to the temperature sensor, and including a cellular communication circuitry, a second processor, and a second memory comprising a second plurality of instructions stored thereon that, in response to execution by the second processor, causes the microcontroller to receive the sensor data from the temperature sensor, determine whether the sensor data is associated with a notification range, establish a cellular communication connection with the server using the cellular communication circuitry in response to a determination that the sensor data is associated with the notification range, and transmit, via the established cellular communication connection, a message to the server indicating that the sensor data is associated with the notification range. In response to execution of the first plurality of instructions by the first processor, the server may be configured to parse the message received from the insulated portable container, generate a notification message indicative of the temperature of the tetanus-containing vaccine based on the parsed message, and transmit the notification message to a mobile device of a vaccination field team.

In some embodiments, to determine whether the sensor data is associated with the notification range may include to analyze the sensor data to estimate whether the temperature of the tetanus-containing vaccine is at a temperature within the notification range, and the notification range may be a range of temperatures of the tetanus-containing vaccine at which the microcontroller is to transmit a warning message to the server.

In some embodiments, the microcontroller may further include a global positioning system (GPS) circuitry, the second plurality of instructions may further cause the microcontroller to receive additional sensor data from the GPS circuitry and determine a location of the insulated portable container based on the additional sensor data of the GPS circuitry, and to transmit the message to the server may include to transmit at least one of the location or the additional sensor data to the server.

In some embodiments, to determine whether the sensor data is associated with the notification range may include to analyze the sensor data to estimate whether a rate of change of the temperature of the tetanus-containing vaccine exceeds a maximum rate of change that allows the insulated portable container to arrive at a target destination without exceeding a temperature limit of the tetanus-containing vaccine based on the determined location of the insulated portable container and a rate of travel of the insulated portable container.

In some embodiments, the second plurality of instructions may further cause the microcontroller to determine whether an update period has expired based on a timer of the microcontroller, establish the cellular communication connection with the server in response to a determination that the update period has expired, and transmit, via the established cellular communication connection, a second message to the server indicative of the temperature of the tetanus-containing vaccine.

In some embodiments, to determine that the sensor data is associated with the notification range may include to determine that the sensor data indicates that the temperature of the tetanus-containing vaccine is less than two degrees Celsius or greater than eight degrees Celsius.

According to another embodiment, an insulated portable container capable of manually transporting vaccines in a temperature-stable environment by a single person may include a housing having a first chamber defined therein that stores one or more vaccines during transport, a buffered temperature sensor container having a second chamber defined therein that houses a buffering agent, a temperature sensor positioned within the buffering agent that generates sensor data representative of a temperature of the one or more vaccines, and a control system secured to the housing, electrically coupled to the temperature sensor, and including a processor and a memory comprising a plurality of instructions stored thereon that, in response to execution by the processor, causes the control system to receive the sensor data from the temperature sensor, determine whether the sensor data is associated with a notification range, establish a long-range wireless communication connection with a server in response to a determination that the sensor data is associated with the notification range, and transmit, via the established long-range wireless communication connection, a message to the server indicating that the sensor data is associated with the notification range.

In some embodiments, to determine whether the sensor data is associated with the notification range may include to analyze the sensor data to estimate whether the temperature of the one or more vaccines is at a temperature within the notification range, and the notification range may be a range of temperatures of the one or more vaccines at which the control system is to transmit a warning message to the server.

In some embodiments, to determine whether the sensor data is associated with the notification range may include to analyze the sensor data to estimate whether a rate of change of the temperature of the one or more vaccines exceeds an expected rate of change.

In some embodiments, the insulated portable container may further include a location sensor, the plurality of instructions may further cause the control system to receive additional sensor data from the location sensor and determine a location of the insulated portable container based on the additional sensor data of the location sensor, and to transmit the message to the server may include to transmit at least one of the location or the additional sensor data to the server.

In some embodiments, to determine whether the sensor data is associated with the notification range may include to analyze the sensor data to estimate whether a rate of change of the temperature of the one or more vaccines exceeds a maximum rate of change that allows the insulated portable container to arrive at a target destination without exceeding a temperature limit of the one or more vaccines based on the determined location of the insulated portable container.

In some embodiments, the plurality of instructions may further cause the control system to determine whether an update period has expired based on a timer of the control system, establish the long-range wireless communication connection with the server in response to a determination that the update period has expired, and transmit, via the established long-range wireless communication connection, a second message to the server indicative of the temperature of the one or more vaccines.

In some embodiments, the server may include or be embodied as a cloud-based virtual server.

In some embodiments, each of the one or more vaccines may be a tetanus-containing vaccine, and to determine that the sensor data is associated with the notification range may include to determine that the sensor data indicates that the temperature of the one or more vaccines is less than two degrees Celsius or greater than eight degrees Celsius.

According to yet another embodiment, a method for monitoring vaccines within an insulated portable container may include receiving, by a control system secured to the insulated portable container, sensor data from a temperature sensor positioned within the insulated portable container, determining, by the control system, whether the sensor data is associated with a notification range, establishing, by the control system, a long-range wireless communication connection with a server in response to a determination that the sensor data is associated with the notification range, and transmitting, by the control system, a message to the server indicating that the sensor data is associated with the notification range in response to establishing the long-range wireless communication connection.

In some embodiments, determining whether the sensor data is associated with the notification range may include analyzing the sensor data to estimate whether a temperature of a vaccine within the insulated portable container is at a temperature within the notification range, and the notification range may be a range of temperatures of the vaccine at which the control system is to transmit a warning message to the server.

In some embodiments, the method may further include receiving, by the control system, additional sensor data from a location sensor of the control system and determining, by the control system, a location of the insulated portable container based on the additional sensor data of the location sensor, and transmitting the message to the server may include transmitting at least one of the location or the additional sensor data to the server.

In some embodiments, establishing the long-range wireless communication connection may include establishing a cellular network connection with the server.

In some embodiments, transmitting the message to the server may include posting the sensor data to the server via a uniform resource identifier (URI) of a notification application programming interface (API) of the server.

According to yet another embodiment, one or more machine-readable medium may include a plurality of instructions stored thereon that, in response to execution by a processor of the control system, causes the control system to receive sensor data from a temperature sensor positioned within the insulated portable container, determine whether the sensor data is associated with a notification range, establish a long-range wireless communication connection with a server in response to a determination that the sensor data is associated with the notification range, and transmit a message to the server indicating that the sensor data is associated with the notification range in response to establishing the long-range wireless communication connection.

Further embodiments, forms, features, and aspects of the present application shall become apparent from the description and figures provided herewith.

BRIEF DESCRIPTION OF THE DRAWINGS

The concepts described herein are illustrative by way of example and not by way of limitation in the accompanying figures. For simplicity and clarity of illustration, elements illustrated in the figures are not necessarily drawn to scale. Where considered appropriate, references labels have been repeated among the figures to indicate corresponding or analogous elements.

DETAILED DESCRIPTION

Although the concepts of the present disclosure are susceptible to various modifications and alternative forms, specific embodiments have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. It should further be appreciated that although reference to a "preferred" component or feature may indicate the desirability of a particular component or feature with respect to an embodiment, the disclosure is not so limiting with respect to other embodiments, which may omit such a component or feature. Further, when a particular feature, structure, or characteristic is described in connection with an embodiment, it is submitted that it is within the knowledge of one skilled in the art to implement such feature, structure, or characteristic in connection with other embodiments whether or not explicitly described. Additionally, it should be appreciated that items included in a list in the form of "at least one of A, B, and C" can mean (A); (B); (C); (A and B); (B and C); (A and C); or (A, B, and C). Similarly, items listed in the form of "at least one of A, B, or C" can mean (A); (B); (C); (A and B); (B and C); (A and C); or (A, B, and C). Further, with respect to the claims, the use of words and phrases such as "a," "an," "at least one," and/or "at least one portion" should not be interpreted so as to be limiting to only one such element unless specifically stated to the contrary, and the use of phrases such as "at least a portion" and/or "a portion" should be interpreted as encompassing both embodiments including only a portion of such element and embodiments including the entirety of such element unless specifically stated to the contrary.

The disclosed embodiments may, in some cases, be implemented in hardware, firmware, software, or a combination thereof. The disclosed embodiments may also be implemented as instructions carried by or stored on one or more transitory or non-transitory machine-readable (e.g., computer-readable) storage media, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures unless indicated to the contrary. Additionally, the inclusion of a structural or method feature in a particular figure is not meant to imply that such feature is required in all embodiments and, in some embodiments, may not be included or may be combined with other features.

Figure 1:
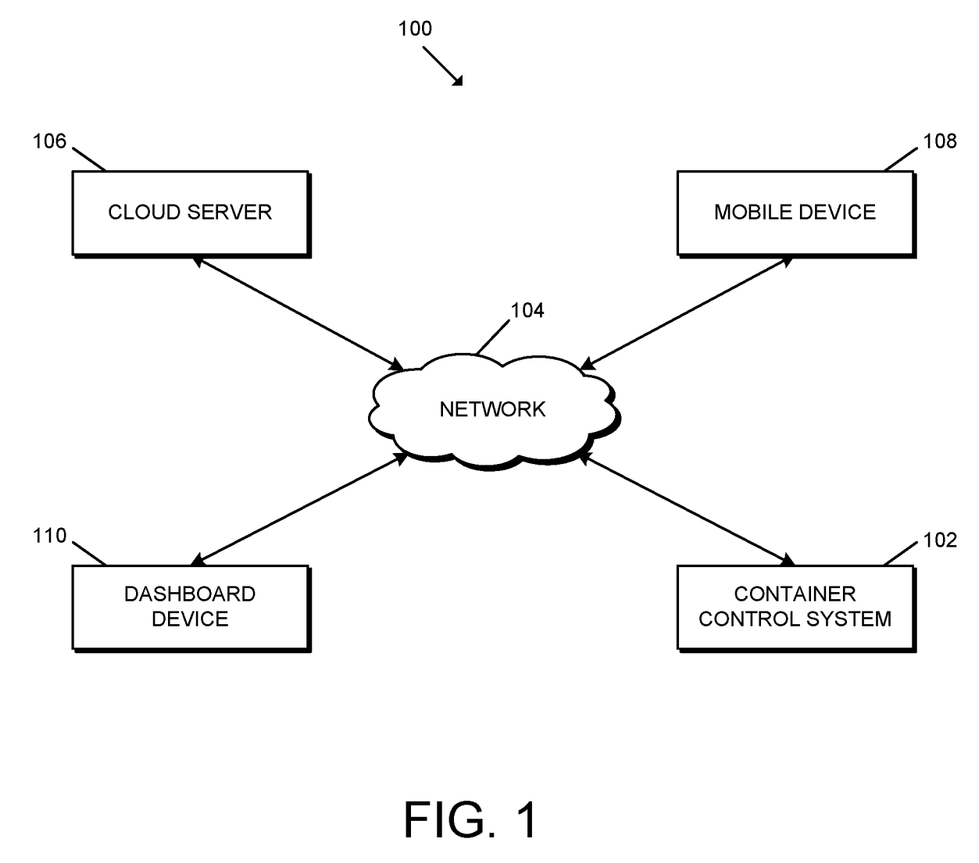
FIG. 1 is a simplified block diagram of at least one embodiment of a vaccine monitoring system.

Referring now to FIG. 1, in the illustrative embodiment, a vaccine monitoring system 100 includes a container control system 102, a network 104, a cloud server 106, a mobile device 108, and a dashboard device 110. As described in detail below, the system 100 allows for the reporting of real-time and/or recent vaccine temperatures, geolocation information of vaccines in-transit, and/or other relevant data to remote devices for notification to and/or data visualization by the relevant parties.

In particular, the container control system 102 may be secured to an insulated portable container (e.g., the container 400 of FIG. 4) for transporting vaccines in a relatively temperature-stable environment and configured to monitor the temperature of the vaccines stored therein. It should be appreciated that the container control system 102 may be embodied as any suitable control system for performing the functions described herein. For example, in the illustrative embodiment, the container control system 102 may include a temperature sensor 318 positioned within the insulated portable container that generates sensor data indicative of a temperature of the vaccines. Further, the container control system 102 may be configured to analyze the sensor data generated by the temperature sensor 318 and/or other sensor data to determine whether to notify the cloud server 106 regarding the current temperature status of the vaccines (e.g., current temperature, expected temperature profile over time, etc.). Additionally, in some embodiments, the container control system 102 may include a global positioning system (GPS) circuitry and/or other location sensor 320 configured to generate data indicative of, or otherwise able to be processed to determine, the location of the container control system 102. For example, in some embodiments, the location sensor 320 may generate data indicative of the longitudinal and latitudinal coordinates of the container control system 102 at a given point in time.

The container control system 102 may establish a long-range wireless communication connection (e.g., via a cellular communication network) with the cloud server 106 to transmit a notification message, status update, sensor data, and/or other suitable information to the cloud server 106. As described below, it should be appreciated that the connection may be established and/or the relevant data/information may be transmitted to the cloud server 106 periodically and/or in response to a particular triggering condition.

It should be appreciated that the cloud server 106 may be embodied as any type of device or collection of devices suitable for performing the functions described herein. More specifically, in the illustrative embodiment, the cloud server 106 may process the data received from the container control system 102, store the received data and/or one or more processed versions thereof, and transmit messages to a mobile device 108 of the vaccination field team and/or other relevant receipt device(s). For example, in some embodiments, the cloud server 106 may generate and transmit a message indicative of the temperature of the tetanus-containing and/or other vaccine(s) stored within the insulated portable container. Further, in some embodiments, the cloud server 106 may utilize the sensor data generated by the location sensor 320 to determine the location of the vaccination field team transporting the insulated portable container, which includes the container control system 102. The vaccination field team may be traveling through geopolitically hostile territories, countries amidst ongoing wars, and remote regions of the world. As such, an implied or determined location of the vaccination field team may be useful in determining whether the team is still en route to the target destination and, if not, whether anticipated conditions within the general region justify involving the local authorities, authorities of the sponsoring organization, an evacuation team, and/or other relevant parties.

It should be further appreciated that, in some embodiments, the cloud server 106 may be embodied as a virtual computing environment residing "on" a computing system (e.g., a distributed network of devices) in which various virtual functions (e.g., Lambda functions, Azure functions, Amazon Web Services cloud functions, Google cloud functions, and/or other suitable virtual functions) may be executed corresponding with the functions of the cloud server 106 described herein. For example, when an event occurs (e.g., data is transferred to the cloud server 106 for handling), the virtual computing environment may be communicated with (e.g., via a request to an API of the virtual computing environment), whereby the API may route the request to the correct virtual function (e.g., a particular server-ambiguous computing resource) based on a set of rules. As such, when a request for the transmission of particular data is made (e.g., via an appropriate interface to the cloud server 106), the appropriate virtual function(s) may be executed to perform the actions before eliminating the instance of the virtual function(s). Although the cloud server 106 is described herein as a cloud-based device, it should be appreciated that the cloud server 106 may be embodied as, or include, one or more servers located "outside" of a cloud computing environment in other embodiments.

The network 104 may be embodied as any type of communication network(s) capable of facilitating communication between the various devices of the system 100. As such, the network 104 may include one or more networks, routers, switches, computers, and/or other intervening devices. For example, the network 104 may be embodied as or otherwise include one or more cellular networks, telephone networks, local or wide area networks, publicly available global networks (e.g., the Internet), ad hoc networks, long-range wireless communication networks, or a combination thereof.

The mobile device 108 may be embodied as any type of computing device that is configured to receive notification messages, sensor data, and/or related information from the cloud server 106 regarding the status of the vaccines within the insulated portable container, the location of the insulated portable container, and/or other information related to the insulated portable container. In some embodiments, the mobile device 108 is configured to receive notification messages from the cloud server 106 via a Short Message Service (SMS) message.

The dashboard device 110 may be embodied as any type of computing device that enables a user to communicate with the cloud server 106 to receive notification messages, sensor data, processed versions of the notification messages and/or sensor data, and/or other relevant information related to one or more portable insulated containers that are in the field. For example, in some embodiments, a user of the dashboard device 110 may execute an application that displays a graphical user interface for visualization of the relevant data (e.g., a smartphone application or a client-side user interface to a web-based application/service of the cloud server 106). In particular, in some embodiments, the user may view data from the various containers in the field (e.g., the vaccine temperature, location, etc.) in real-time (or near real-time), view historical data related to the containers, and/or generate reports. Further, in some embodiments, the user may filter the visualized data based on suitable parameters (e.g., by critical events, geolocation, etc.). It should further be appreciated that, in some embodiments, the particular data viewable by the user may vary depending on the role of the user (e.g., field operations team, field operations manager, business analyst, system engineer, local authorities, etc.). For example, if the last reported location of a particular container has not moved after a predetermined period of time (e.g., two hours) and the container is expected to be in active transit, such information may be available to local authorities as a warning but may be unavailable to other roles. Additionally, in an embodiment in which thousands of vaccination field teams are in the field, a user monitoring the teams may filter the data to view only critical issues (e.g., vaccine temperature nearing/surpassing limits) and/or containers within certain geographical locations/regions.

As described in detail, in the illustrative embodiment, the container control system 102 may communicate with the cloud server 106 using any suitable long-range wireless communication (e.g., via a cellular network). It should be appreciated that such long-range wireless communication excludes Wi-Fi, Bluetooth, and other near-range communication. However, in the illustrative embodiment, the cloud server 106 may communicate with the mobile device 108 and/or the dashboard device 110 using any suitable communication connection.

It should be appreciated that each of the cloud server 106, the mobile device 108, and/or the dashboard device 110 may be embodied as a computing device similar to the computing device 200 described below in reference to FIG. 2. For example, in the illustrative embodiment, each of the cloud server 106, the mobile device 108, and the dashboard device 110 includes a processing device 202 and a memory 206 having stored thereon operating logic 208 for execution by the processing device 202 for operation of the corresponding device. Additionally, it should be appreciated that the container control system 102 may include features similar to the features described below in reference to the computing device 200 of FIG. 2.

Although only container control system 102, one cloud server 106, one mobile device 108, and one dashboard device 110 are shown in the illustrative embodiment of FIG. 1, the vaccine monitoring system 100 may include multiple container control systems 102, cloud servers 106, mobile devices 108, and/or dashboard devices 110 in other embodiments. For example, as described herein, a user of a particular dashboard device 110 may visualize data representative of multiple insulated portable containers and, therefore, multiple container control systems 102. Similarly, multiple mobile devices 108 may receive notification messages from the cloud server 106 providing a status update for a corresponding insulated portable container.

Figure 2:
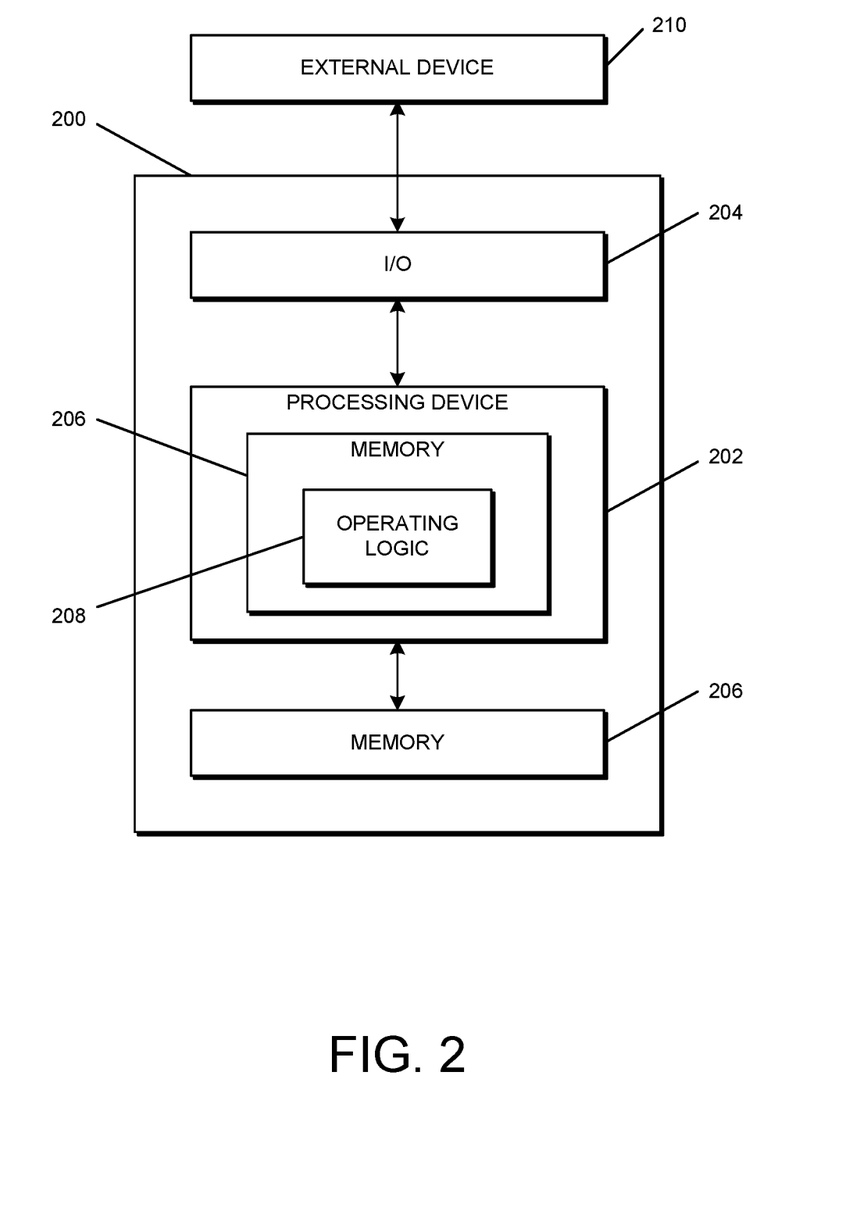
FIG. 2 is a simplified block diagram of at least one embodiment of a computing system.

Referring now to FIG. 2, a simplified block diagram of at least one embodiment of a computing device 200 is shown. The illustrative computing device 200 depicts at least one embodiment of a cloud server, mobile device, and/or dashboard device that may be utilized in connection with the cloud server 106, the mobile device 108, and/or the dashboard device 110 illustrated in FIG. 1. Depending on the particular embodiment, the computing device 200 may be embodied as a server, desktop computer, laptop computer, tablet computer, notebook, netbook, Ultrabook™, mobile computing device, cellular phone, smartphone, wearable computing device, personal digital assistant, Internet of Things (IoT) device, processing system, router, gateway, and/or any other computing, processing, and/or communication device capable of performing the functions described herein.

The computing device 200 includes a processing device 202 that executes algorithms and/or processes data in accordance with operating logic 208, an input/output device 204 that enables communication between the computing device 200 and one or more external devices 210, and memory 206 which stores, for example, data received from the external device 210 via the input/output device 204.

The input/output device 204 allows the computing device 200 to communicate with the external device 210. For example, the input/output device 204 may include a transceiver, a network adapter, a network card, an interface, one or more communication ports (e.g., a USB port, serial port, parallel port, an analog port, a digital port, VGA, DVI, HDMI, FireWire, CAT 5, or any other type of communication port or interface), and/or other communication circuitry. Communication circuitry of the computing device 200 may be configured to use any one or more communication technologies (e.g., wireless or wired communications) and associated protocols (e.g., Ethernet, Bluetooth®, Wi-Fi®, WiMAX, etc.) to effect such communication depending on the particular computing device 200. The input/output device 204 may include hardware, software, and/or firmware suitable for performing the techniques described herein.

The external device 210 may be any type of device that allows data to be inputted or outputted from the computing device 200. For example, in various embodiments, the external device 210 may be embodied as the container control system 102, the cloud server 106, the mobile device 108, and/or the dashboard device 110. Further, in some embodiments, the external device 210 may be embodied as another computing device, switch, diagnostic tool, controller, printer, display, alarm, peripheral device (e.g., keyboard, mouse, touch screen display, etc.), and/or any other computing, processing, and/or communication device capable of performing the functions described herein. Furthermore, in some embodiments, it should be appreciated that the external device 210 may be integrated into the computing device 200.

The processing device 202 may be embodied as any type of processor(s) capable of performing the functions described herein. In particular, the processing device 202 may be embodied as one or more single or multi-core processors, microcontrollers, or other processor or processing/controlling circuits. For example, in some embodiments, the processing device 202 may include or be embodied as an arithmetic logic unit (ALU), central processing unit (CPU), digital signal processor (DSP), and/or another suitable processor(s). The processing device 202 may be a programmable type, a dedicated hardwired state machine, or a combination thereof. Processing devices 202 with multiple processing units may utilize distributed, pipelined, and/or parallel processing in various embodiments. Further, the processing device 202 may be dedicated to performance of just the operations described herein, or may be utilized in one or more additional applications. In the illustrative embodiment, the processing device 202 is programmable and executes algorithms and/or processes data in accordance with operating logic 208 as defined by programming instructions (such as software or firmware) stored in memory 206. Additionally or alternatively, the operating logic 208 for processing device 202 may be at least partially defined by hardwired logic or other hardware. Further, the processing device 202 may include one or more components of any type suitable to process the signals received from input/output device 204 or from other components or devices and to provide desired output signals. Such components may include digital circuitry, analog circuitry, or a combination thereof.

The memory 206 may be of one or more types of non-transitory computer-readable media, such as a solid-state memory, electromagnetic memory, optical memory, or a combination thereof. Furthermore, the memory 206 may be volatile and/or nonvolatile and, in some embodiments, some or all of the memory 206 may be of a portable type, such as a disk, tape, memory stick, cartridge, and/or other suitable portable memory. In operation, the memory 206 may store various data and software used during operation of the computing device 200 such as operating systems, applications, programs, libraries, and drivers. It should be appreciated that the memory 206 may store data that is manipulated by the operating logic 208 of processing device 202, such as, for example, data representative of signals received from and/or sent to the input/output device 204 in addition to or in lieu of storing programming instructions defining operating logic 208. As shown in FIG. 2, the memory 206 may be included with the processing device 202 and/or coupled to the processing device 202 depending on the particular embodiment. For example, in some embodiments, the processing device 202, the memory 206, and/or other components of the computing device 200 may form a portion of a system-on-a-chip (SoC) and be incorporated on a single integrated circuit chip.

In some embodiments, various components of the computing device 200 (e.g., the processing device 202 and the memory 206) may be communicatively coupled via an input/output subsystem, which may be embodied as circuitry and/or components to facilitate input/output operations with the processing device 202, the memory 206, and other components of the computing device 200. For example, the input/output subsystem may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations.

The computing device 200 may include other or additional components, such as those commonly found in a typical computing device (e.g., various input/output devices and/or other components), in other embodiments. It should be further appreciated that one or more of the components of the computing device 200 described herein may be distributed across multiple computing devices. In other words, the techniques described herein may be employed by a computing system that includes one or more computing devices. Additionally, although only a single processing device 202, I/O device 204, and memory 206 are illustratively shown in FIG. 2, it should be appreciated that a particular computing device 200 may include multiple processing devices 202, I/O devices 204, and/or memories 206 in other embodiments. Further, in some embodiments, more than one external device 210 may be in communication with the computing device 200.

Figure 3:
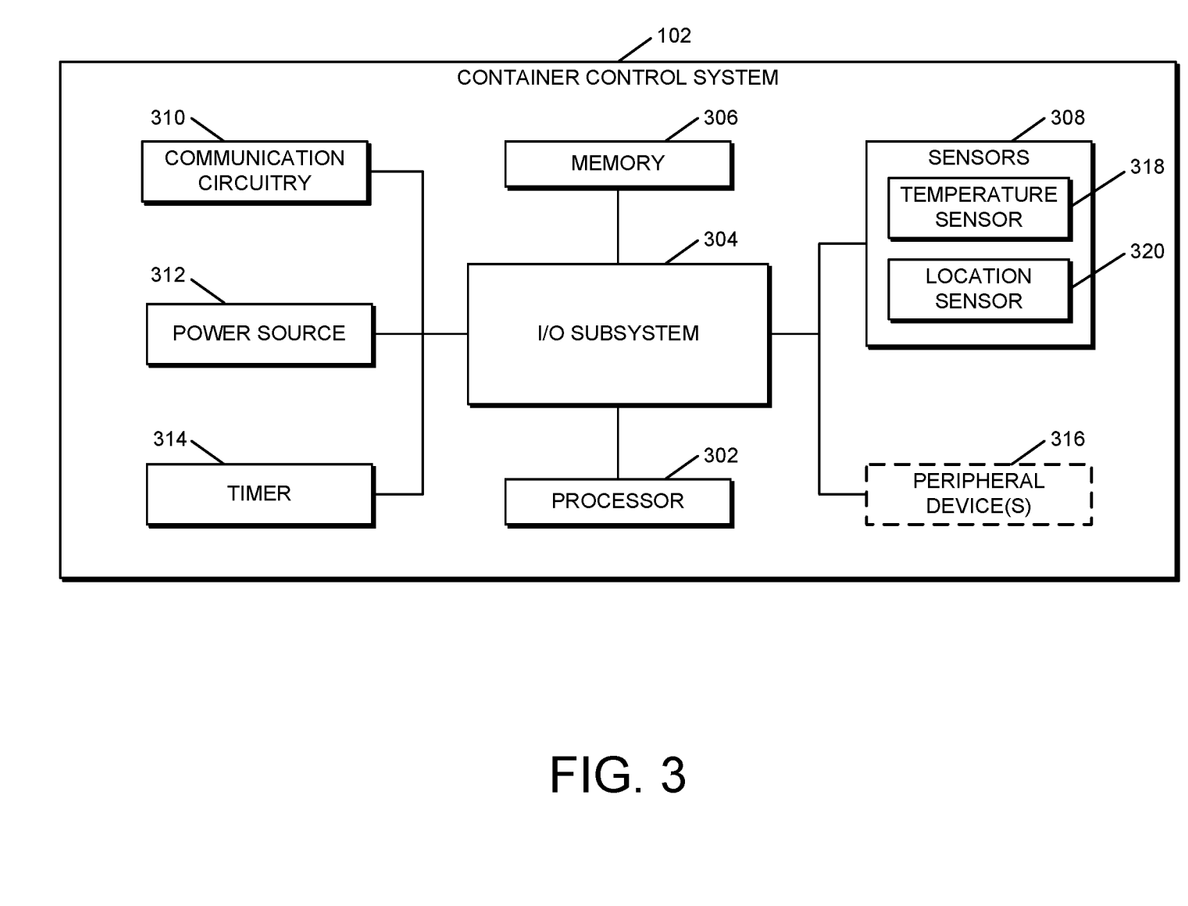
FIG. 3 is a simplified block diagram of at least one embodiment of the container control system of FIG. 1.

Referring now to FIG. 3, a simplified block diagram of at least one embodiment of the container control system 102 is shown. The illustrative container control system 102 includes a processor 302, an input/output ("I/O") subsystem 304, a memory 306, one or more sensors 308, communication circuitry 310, power source 312, and a timer 314. Further, in some embodiments, the container control system 102 may include one or more peripheral devices 316. It should be appreciated that one or more of the components of the container control system 102 described herein may be embodied as, or form a portion of, one or more embedded controllers and/or integrated circuits of an insulated portable container. For example, in some embodiments, the processor 302, the I/O subsystem 304, the memory 306 and/or other components of the container control system 102 may be embodied as, or form a portion of, a microcontroller or SoC. Further, depending on the particular embodiment, the components of the container control system 102 may be closely positioned to one another or distributed throughout the insulated portable container (i.e., separated from one another).

The processor 302 may be embodied as any type of processor(s) capable of performing the functions described herein. In particular, the processor 302 may be embodied as one or more single or multi-core processors, microcontrollers, or other processor or processing/controlling circuits. For example, in some embodiments, the processor 302 may include or be embodied as an arithmetic logic unit (ALU), central processing unit (CPU), digital signal processor (DSP), and/or another suitable processor(s). The processor 302 may be a programmable type, a dedicated hardwired state machine, or a combination thereof. One or more processors 302 with multiple processing units may utilize distributed, pipelined, and/or parallel processing in various embodiments. Further, the processor 302 may be dedicated to performance of just the operations described herein, or may be utilized in one or more additional applications. In the illustrative embodiment, the processor 302 is of a programmable variety that executes algorithms and/or processes data in accordance with operating logic as defined by programming instructions (such as software or firmware) stored in the memory 306. Additionally or alternatively, the operating logic for the processor 302 may be at least partially defined by hardwired logic or other hardware. Further, the processor 302 may include one or more components of any type suitable to process the signals received from input/output devices or from other components or devices and to provide desired output signals. Such components may include digital circuitry, analog circuitry, or a combination thereof.

The memory 306 may be of one or more types of non-transitory computer-readable media, such as a solid-state memory, electromagnetic memory, optical memory, or a combination thereof. Furthermore, the memory 306 may be volatile and/or nonvolatile and, in some embodiments, some or all of the memory 306 may be of a portable variety, such as a disk, tape, memory stick, cartridge, and/or other suitable portable memory. In operation, the memory 306 may store various data and software used during operation of the container control system 102 such as operating systems (e.g., real-time operating systems (RTOS)), applications, programs, libraries, and drivers. The memory 306 is communicatively coupled to the processor 302 via the I/O subsystem 304, which may be embodied as circuitry and/or components to facilitate input/output operations with the processor 302, the memory 306, and other components of the container control system 102. For example, the I/O subsystem 304 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. Depending on the particular embodiment, the memory 306 may be included with the processor 302 and/or coupled to the processor 302 depending on the particular embodiment. For example, in some embodiments, the processor 302, the I/O subsystem 304, the memory 306, and/or other components of the container control system 102 may form a portion of a system-on-a-chip (SoC) and be incorporated on a single integrated circuit chip.

The sensors 308 are configured to generate sensor data (e.g., by virtue of one or more signals), which may be interpreted by the processor 302 to determine one or more characteristics associated with the container control system 102 and/or the associated insulated portable container. By way of example, the sensors 308 may detect various characteristics of the physical environment of the associated insulated portable container (internal and/or external to the container) and/or other suitable characteristics. In particular, in the illustrative embodiment, the sensors 308 include at least one temperature sensor 318 and at least one location sensor 320. In some embodiments, one or more of the sensors 308 (e.g., the temperature sensor 318) is waterproof and/or water resistant.

The temperature sensor 318 may be configured to generate sensor data representative of a temperature within the insulated portable container. More specifically, in the illustrative embodiment, the temperature sensor 318 is positioned within a buffering agent and configured to generate sensor data representative of the temperature of the tetanus-containing vaccines and/or other vaccines stored within the container (see, e.g., the insulated portable container 400 of FIG. 4).

The location sensor 320 may be configured to generate data indicative of, or otherwise able to be processed to determine, the location of the container control system 102. More specifically, in some embodiments, the location sensor 320 may be embodied as, or form a portion of, a GPS circuitry. Further, as indicated above, the location sensor 320 may generate data indicative of the longitudinal and latitudinal coordinates of the container control system 102 at a given point in time. It should be appreciated, however, that the location sensor 320 may otherwise represent the location of the container control system 102 in other embodiments.

It should be appreciated that the sensors 308 may be embodied as, or otherwise include, other sensors in other embodiments. For example, in various embodiments, the sensors 308 may be embodied as, or otherwise include, other environmental sensors, inertial sensors, proximity sensors, optical sensors, electromagnetic sensors, audio sensors, motion sensors, piezoelectric sensors, cameras, and/or other types of sensors. It should be appreciated that, in some embodiments, additional and/or alternative sensors 308 other than those described above may be included in the container control system 102. Of course, the container control system 102 may also include components and/or devices configured to facilitate the use of the sensors 308.

The communication circuitry 310 may be embodied as any communication circuitry, transceiver, device, or collection thereof, capable of enabling long-range wireless communication between the container control system 102 and other remote devices (e.g., the cloud server 106). The communication circuitry 310 may be configured to use any one or more long-range wireless communication technologies and associated protocols. For example, in the illustrative embodiment, the container control system 102 is configured to communicate over a cellular communication network. In other embodiments, the container control system 102 may be configured to communicate using satellite communication (e.g., via geosynchronous or low Earth orbit (LEO) satellite systems) and/or another suitable long-range communication technology.

The power source 312 is an independent, untethered, and portable power source configured to supply power to the container control system 102 to perform the various functions described herein. For example, the power source 312 may include one or more batteries, battery packs, capacitors, super capacitors, solar cells, and/or other power supplies. Depending on the particular embodiment, the power source 312 may or may not be rechargeable.

The timer 314 is configured to track the amount of time that has lapsed using a suitable mechanism (e.g., clock cycles of the processor 302). For example, in some embodiments, the timer 314 may be embodied as a real-time clock. As described below, the timer 314 may be used to determine, for example, the amount of time that has lapsed since the last transmission of a status update regarding the temperature of the vaccines within the insulated portable container to the cloud server 106.

The peripheral devices 316 may include any number of additional peripheral or interface devices. For example, in some embodiments, the peripheral devices 316 may include a keyboard, mouse, display, status indicator, diagnostic took, speaker, microphone, and/or one or more other suitable peripheral devices.

It should be appreciated that the container control system 102 may include additional or alternative components, such as those commonly found in an embedded control system, for example, in other embodiments. Further, in some embodiments, one or more of the components of the container control system 102 described herein may be omitted from the container control system 102 of a particular insulated portable container (e.g., peripheral devices 316).

It should be further appreciated that the insulated portable container described herein may be embodied as any type of container having a chamber capable of storing one or more vaccines (e.g., tetanus-containing vaccines), insulated to help ensure a relatively temperature-stable environment during transmit, and sized to be manually portable by a single person (e.g., less than four cubic feet in size). In particular, in some embodiments, the insulated portable container may be embodied as a container similar to the insulated portable container 400 of FIG. 4. As shown, the insulated portable container 400 includes a housing 402 having a first chamber 404 defined therein for storage and transport of the vaccines 406 (e.g., tetanus-containing vaccines). Although the housing 402 of the insulated portable container 400 is illustrated as being generally cylindrical in shape, and the illustrative first chamber 404 is similarly generally cylindrical in shape, it should be appreciated that the housing 402 and/or the first chamber 404 may have any other shape suitable for performing the functions described herein.

Figure 4:
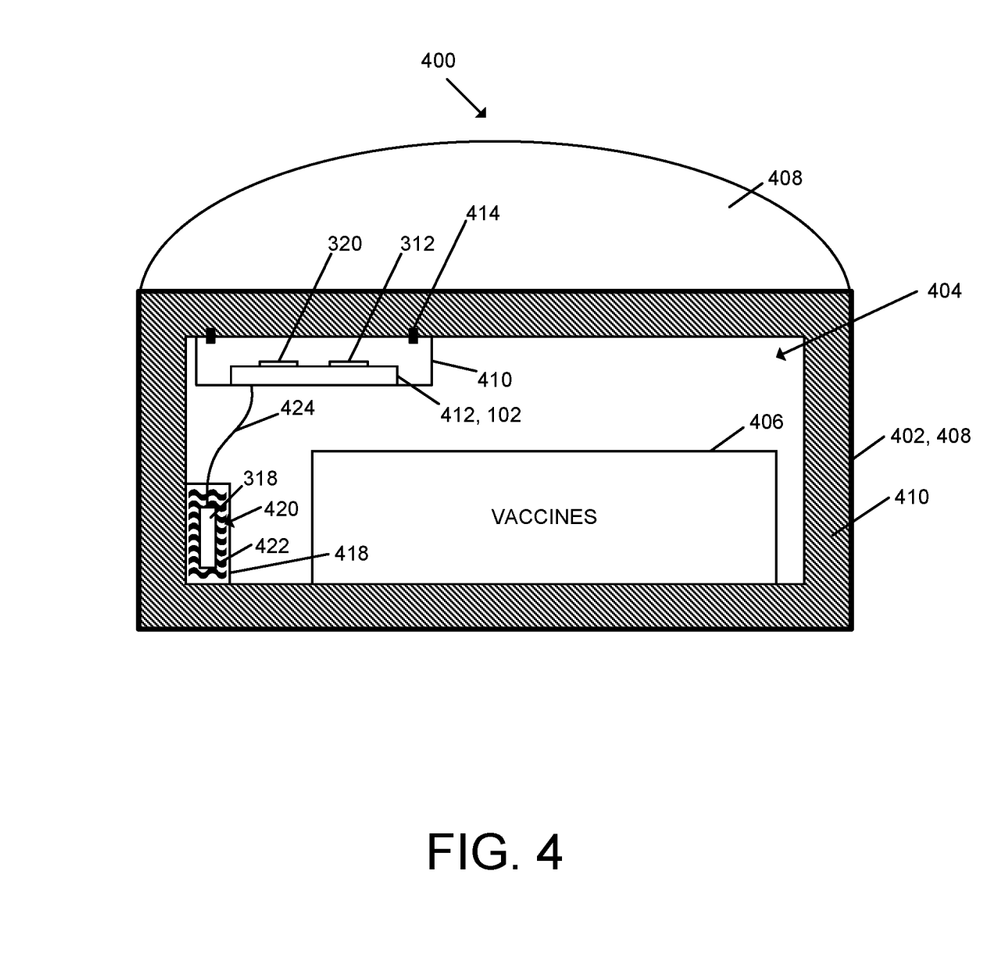
FIG. 4 is a simplified cross-sectional perspective view of at least one embodiment of an insulated portable container including the container control system of FIG. 1.

As shown in FIG. 4, the illustrative housing 402 is defined by hard shell walls 408, and an insulation layer 410 is secured to an interior side of the hard shell walls 408. In some embodiments, the insulation layer 410 may form a portion of the housing 402, whereas in other embodiments, the insulation layer 410 may be one or more separate components. For example, in some embodiments, Styrofoam and/or other suitable insulation material may be placed or secured to the interior side of the hard shell walls 408 (e.g., covering every interior portion of the walls 408). Further, it should be appreciated that, in some embodiments, one or more of the hard shell walls 408 may itself be composed of one or more insulating materials. The hard shell walls 408 and the insulation layer 410 serve to protect the vaccines 406 and help ensure that the first chamber 404 is a relatively temperature-stable region, although exposure to environments at varying temperatures may result in the internal temperature of the first chamber 404 and, therefore, the vaccines 406 to change over time.

In the illustrative insulated portable container 400, the container control system 102 is embodied as a microcontroller 412 and includes a battery as the power source 312 and cellular communication circuitry as the communication circuitry 310. Additionally, as shown, the microcontroller 412 is mounted to a microcontroller housing 414, which is secured to the insulation layer 410, one or more of the hard shell walls 408, and/or the housing 402 via one or more suitable fastening mechanisms 416. As shown, the illustrative insulated portable container 400 includes a buffered temperature sensor container 418 that defines a second chamber 420 for housing a buffering agent 422. In the illustrative embodiment, the temperature sensor 318 is electrically coupled to the microcontroller 412 via an electrical coupling 424, positioned within the buffering agent 422, and configured to generate sensor data representative of the temperature of the vaccines 406. It should be appreciated that the buffering agent 422 serves to simulate the physics that the vaccines 406 undergo in the container 400 with respect to temperature changes (e.g., accounting for differences in the rate of temperature change in ambient air within the first chamber 404 and the rate of change within the liquid vaccines 406). In some embodiments, the buffering agent 422 may be embodied as or include sand, glass beads, glycol propylene, and/or another suitable buffering agent for performing the functions described herein.

Figure 5:
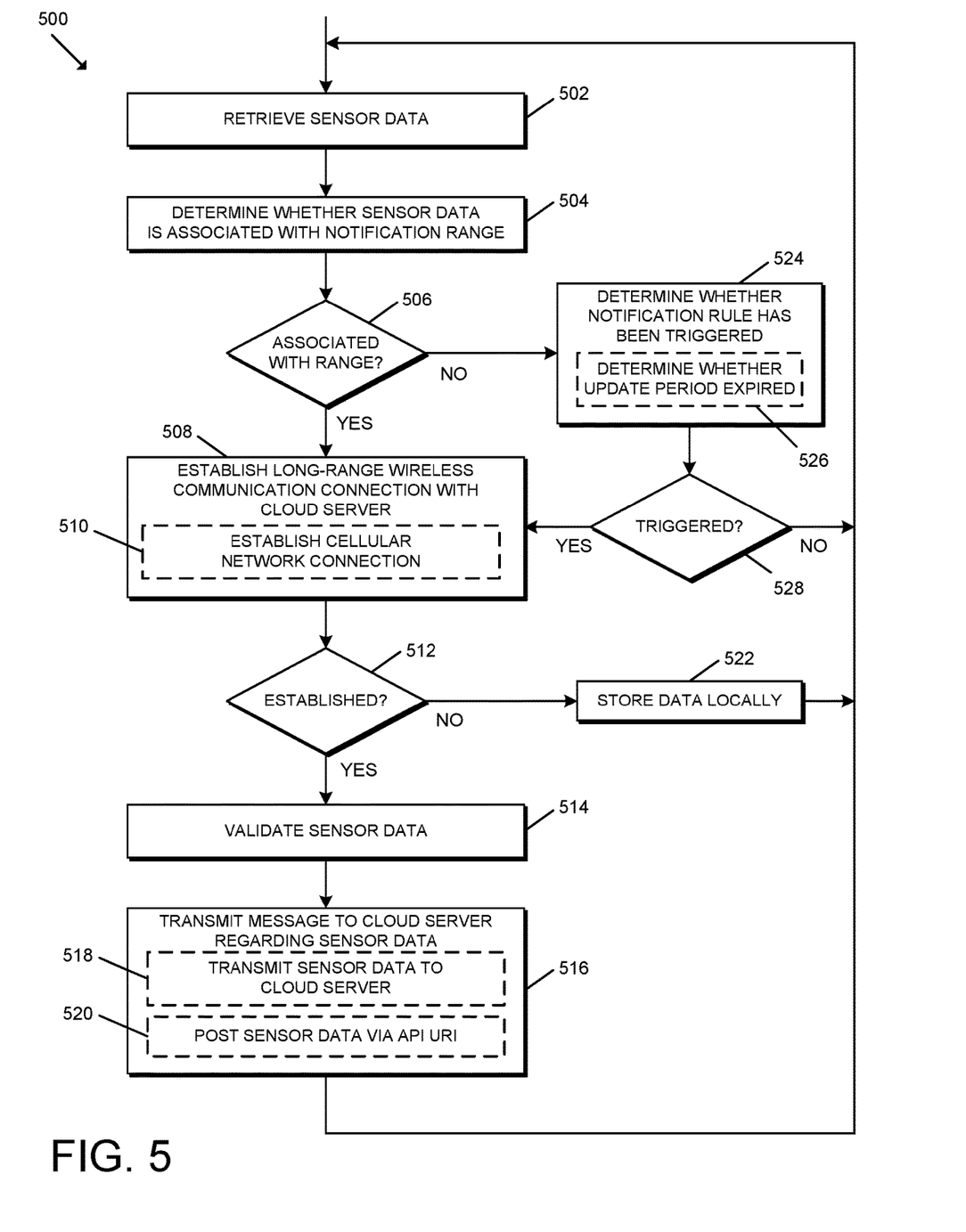
FIG. 5 is a simplified flow diagram of at least one embodiment of a method for monitoring vaccines within an insulated portable container using the container control system of FIG. 1.

Referring now to FIG. 5, in use, the vaccine monitoring system 100 or, more specifically, the container control system 102 may execute a method 500 for monitoring vaccines within an insulated portable container (e.g., the insulated portable container 400 of FIG. 4). It should be appreciated that the particular blocks of the method 500 are illustrated by way of example, and such blocks may be combined or divided, added or removed, and/or reordered in whole or in part depending on the particular embodiment, unless stated to the contrary. The illustrative method 500 begins with block 502 in which the container control system 102 retrieves sensor data generated by one or more sensors 308 of the container control system 102. In particular, in some embodiments, the container control system 102 may retrieve sensor data previously stored locally to the memory 306 of the system 102. For example, in some embodiments, the container control system 102 may execute a method 600 of FIG. 6 as described below for validating and locally storing streamed sensor data for subsequent retrieval. As described above, the container control system 102 retrieve sensor data generated by the temperature sensor 318 and, in some embodiments, also retrieves sensor data generated by the location sensor 320 and/or other sensors 308.

In block 504, the container control system 102 determines whether the sensor data is associated with a notification range. In particular, in some embodiments, the container control system 102 may analyze the temperature sensor data to determine whether the temperature of the vaccines is at a temperature within a notification range. It should be appreciated that a notification range may be a range of temperatures that, when identified/observed by the container control system 102, the container control system 102 is to transmit a warning or other message to the cloud server 106. For example, tetanus-containing vaccines may be required to be maintained within a temperature range of 2-8° Celsius, and if the vaccine temperatures go beyond those limits, the vaccines may no longer be effective. It should be appreciated that other vaccines may similarly have predefined temperature ranges within which the vaccines must be maintained to avoid spoilage. Accordingly, in some embodiments, the container control system 102 may analyze the temperature sensor data to determine whether the temperature sensor data indicates that the temperature of the tetanus-containing vaccine is less than 2° Celsius (a notification range) or greater than 8° Celsius (another notification range). As such, the container control system 102 may transmit a message that indicates the vaccines have likely already been ruined based on the temperature.

Further, in some embodiments, it should be appreciated that the container control system 102 may utilize multiple notification ranges to represent different conditions or temperatures of concern. For example, the container control system 102 may utilize notification ranges that are nearing the temperature limits for a particular vaccine to warn the cloud server 106 and, therefore, the vaccination field team and/or other relevant parties of the imminent concern regarding vaccine temperature (e.g., 2-3° Celsius and/or 7-8° Celsius in the case of tetanus-containing vaccines).

In other embodiments, the container control system 102 may analyze the temperature sensor data to determine a rate of change of the temperature of the vaccines and, for example, estimate whether the rate of change of the vaccine temperature exceeds an expected rate of change (e.g., under environmental conditions anticipated for the particular journey). More specifically, the container control system 102 may use a sliding window algorithm that calculates the average temperature over the window (e.g., 30 samples) and determine whether the rate of temperature change exceeds that considered to be normal. It should be appreciated that "normal" may be defined based on the distance left to be traversed and the rate of travel. For example, in some embodiments, the container control system 102 may analyze sensor data generated by the location sensor 320 (e.g., GPS circuitry) and determine the location of the insulated portable container based on the location sensor data. The container control system 102 may further determine a maximum rate of change of temperature of the vaccines that allows the insulated portable container to arrive at the target destination of the vaccination field team based on the location of the container (i.e., based on the distance between the current location of the container and the target destination) without exceeding a temperature limit of the vaccines, and the control system 102 may determine whether the rate of change of the vaccine temperature exceeds that maximum rate. In other embodiments, it should be appreciated that the container control system 102 may monitor for the occurrence of one or more other events/conditions in block 504.

If the container control system 102 determines, in block 506, that the sensor data is associated with one or more notification ranges, the method 500 advances to block 508 in which the container control system 102 establishes a long-range wireless communication connection with the cloud server 106. For example, in block 510, the container control system 102 may establish a cellular network connection with the cloud server 106 in some embodiments. If the container control system 102 determines, in block 512, that a connection has been established, the method 500 advances to block 514 in which the container control system 102 may further validate the sensor data before transmitting a message to the cloud server 106. It should be appreciated that the container control system 102 may validate the sensor data in a manner similar to that described below in reference to block 604 of FIG. 6.

If block 514 is performed, assuming the sensor data is determined to be valid, the container control system 102 transmits a message to the cloud server 106 regarding the sensor data in block 516. In particular, the container control system 102 may transmit a message indicating that the sensor data is associated with the notification range and/or another condition that elicited establishing the communication connection. Further, in block 518, the container control system 102 may transmit the sensor data (e.g., temperature sensor data, location sensor data, etc.), derived/processed data (e.g., the determined location of the container), and/or other relevant data to the cloud server 106. In some embodiments, in block 520, the container control system 102 may post the message and/or the sensor data to the cloud server 106 via a uniform resource identifier (URI) of a notification application programming interface (API) of the cloud server 106.

After transmitting the message and/or sensor data to the cloud server 106, the method 500 returns to block 502 in which the container control system 102 retrieves new sensor data for processing according to the method 500. In some embodiments, it should be appreciated that the container control system 102 may disconnect the established long-range wireless communication connection with the cloud server 106 subsequent to transmission of the message and/or sensor data, for example, in order to conserve power. As such, in some embodiments, the communication circuitry 310 may be in a sleep state unless awakened to transmit data to the cloud server 106.

Returning to block 512, if the container control system 102 is unable to establish a long-range wireless communication connection with the cloud server 106, the container control system 102 may store the relevant data locally in block 522. For example, in some embodiments, the container control system 102 may store a message to be transmitted to the cloud server 106 once such a connection is established. Further, any derived/processed and/or sensor data not already stored may also be stored locally.

Returning to block 506, if the container control system 102 determines that the sensor data is not associated with a notification range, the method 500 advances to block 524 in which the container control system 102 determines whether a notification rule has been triggered. For example, in some embodiments, the container control system 102 may periodically transmit an update message regarding the status of the insulated portable container to the cloud server 106 (e.g., including the current temperature, location, and/or associated sensor data), which may be forwarded to the vaccination field team. As such, in block 526, the container control system 102 may determine whether an update period has expired based on the timer 314. In other embodiments, it should be appreciated that the container control system 102 may utilize additional or alternative notification rules. If the container control system 102 determines, in block 528, that a notification rule has been triggered, the method 500 advances to block 508 in which the container control system 102 establishes a long-range wireless communication connection with the cloud server 106 and transmits a message to the cloud server 106 as described above. Otherwise, the method 500 returns to block 502 in which the container control system 102 retrieves new sensor data for processing according to the method 500.

Although described as being performed by the container control system 102 in the illustrative embodiment, it should be appreciated that one or more of the functions described herein may be performed by the cloud server 106 in other embodiments. Further, although the blocks 502-528 are described in a relatively serial manner, it should be appreciated that various blocks of the method 500 may be performed in parallel in some embodiments.

Figure 6:
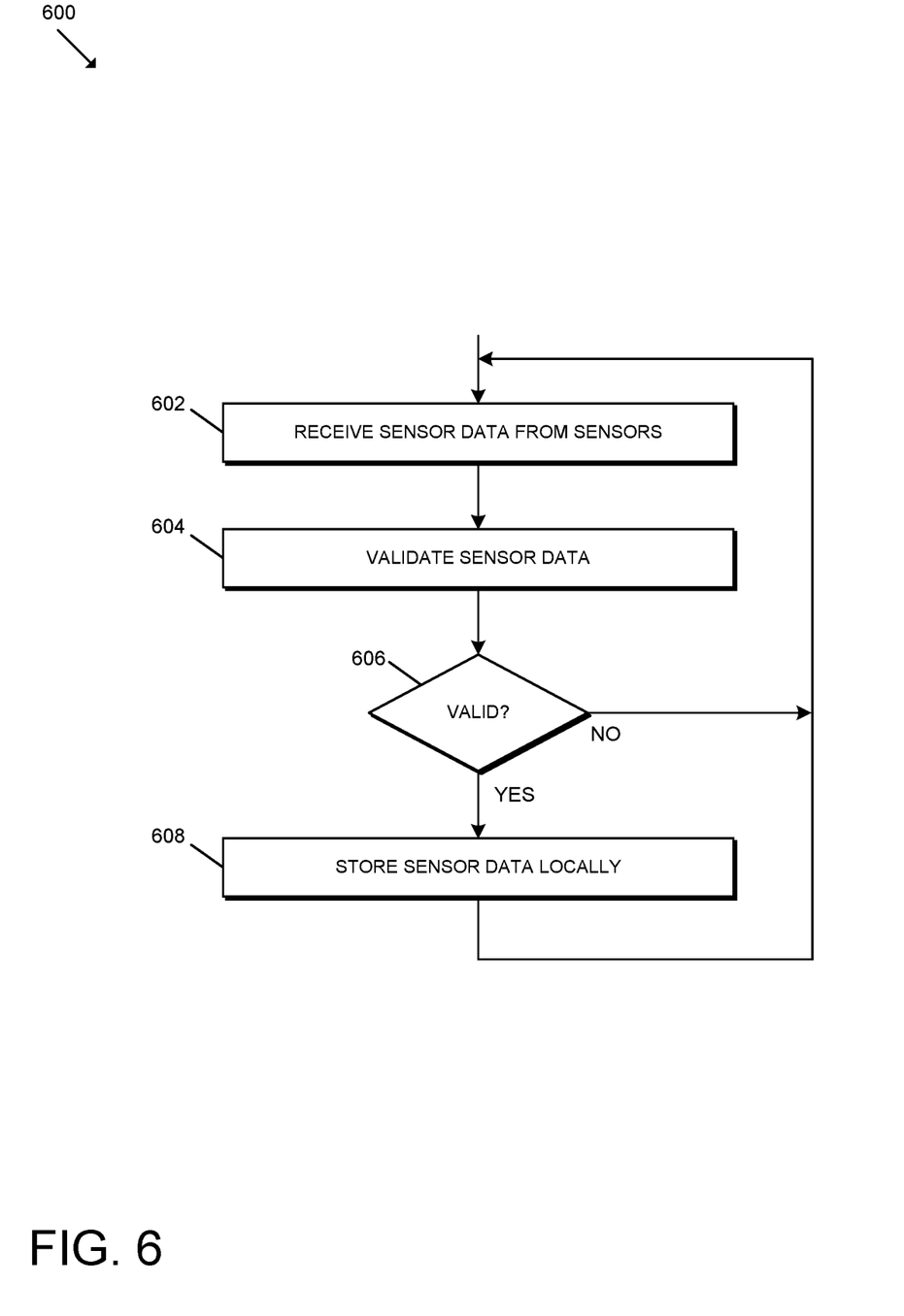
FIG. 6 is a simplified flow diagram of at least one embodiment of a method for locally storing streamed sensor data using the container control system of FIG. 1.

Referring now to FIG. 6, in use, the vaccine monitoring system 100 or, more specifically, the container control system 102 may execute a method 600 for locally storing streamed sensor data. It should be appreciated that the particular blocks of the method 600 are illustrated by way of example, and such blocks may be combined or divided, added or removed, and/or reordered in whole or in part depending on the particular embodiment, unless stated to the contrary. The illustrative method 600 begins with block 602 in which the container control system 102 receives sensor data from the sensors 308. For example, in some embodiments, the container control system 102 receives sensor data generated by the temperature sensor 318, the location sensor 320, and/or one or more other sensors 308. It should be appreciated that, in some embodiments, the container control system 102 receives the sensor data in the form of one or more data streams.

In block 604, the container control system 102 determines whether the received sensor data is valid. In particular, in some embodiments, the container control system 102 may confirm that the temperature represented by the sensor data generated by the temperature sensor 318 is within a temperature range that is to be expected. For example, in some embodiments, the container control system 102 may confirm that the temperature is not below 0° Celsius or at another extreme temperature. Additionally, the container control system 102 may confirm that no hardware errors occurred (e.g., no cyclic redundancy check (CRC) errors occurred). Further, in some embodiments, the container control system 102 may confirm that the received sensor data is in the proper format expected (e.g., floating point values). The container control system 102 may also validate the sensor data generated by the location sensor 320 (e.g., GPS data). For example, the container control system 102 may determine whether longitudinal and latitudinal coordinates indicated by the location sensor data are representative of the same general region that the corresponding vaccination field team is believed to be operating (e.g., within the same continent or sub-continent).

If the container control system 102 determines, in block 606, that the sensor data is valid, the method 600 advances to block 608 in which the container control system 102 stores the validated sensor data locally in the memory 306. As described above, the sensor data may be subsequently retrieved by the container control system 102 for analysis. The method 600 returns to block 602 in which the container control system 102 receives and validates the new sensor data from the sensor data stream(s). Returning to block 606, if the container control system 102 determines the sensor data to be invalid, the container control system 102 may discard the data or perform another suitable error handling procedure. Further, the method 600 returns to block 602 in which the container control system 102 receives and validates the new sensor data from the sensor data stream(s). In other words, the container control system 102 validates and stores data received from the sensors 308 in real time such that it can be subsequently processed by the container control system 102 as described above (e.g., in real time or near real time).

Although the blocks 602-608 are described in a relatively serial manner, it should be appreciated that various blocks of the method 600 may be performed in parallel in some embodiments.

Figure 7:
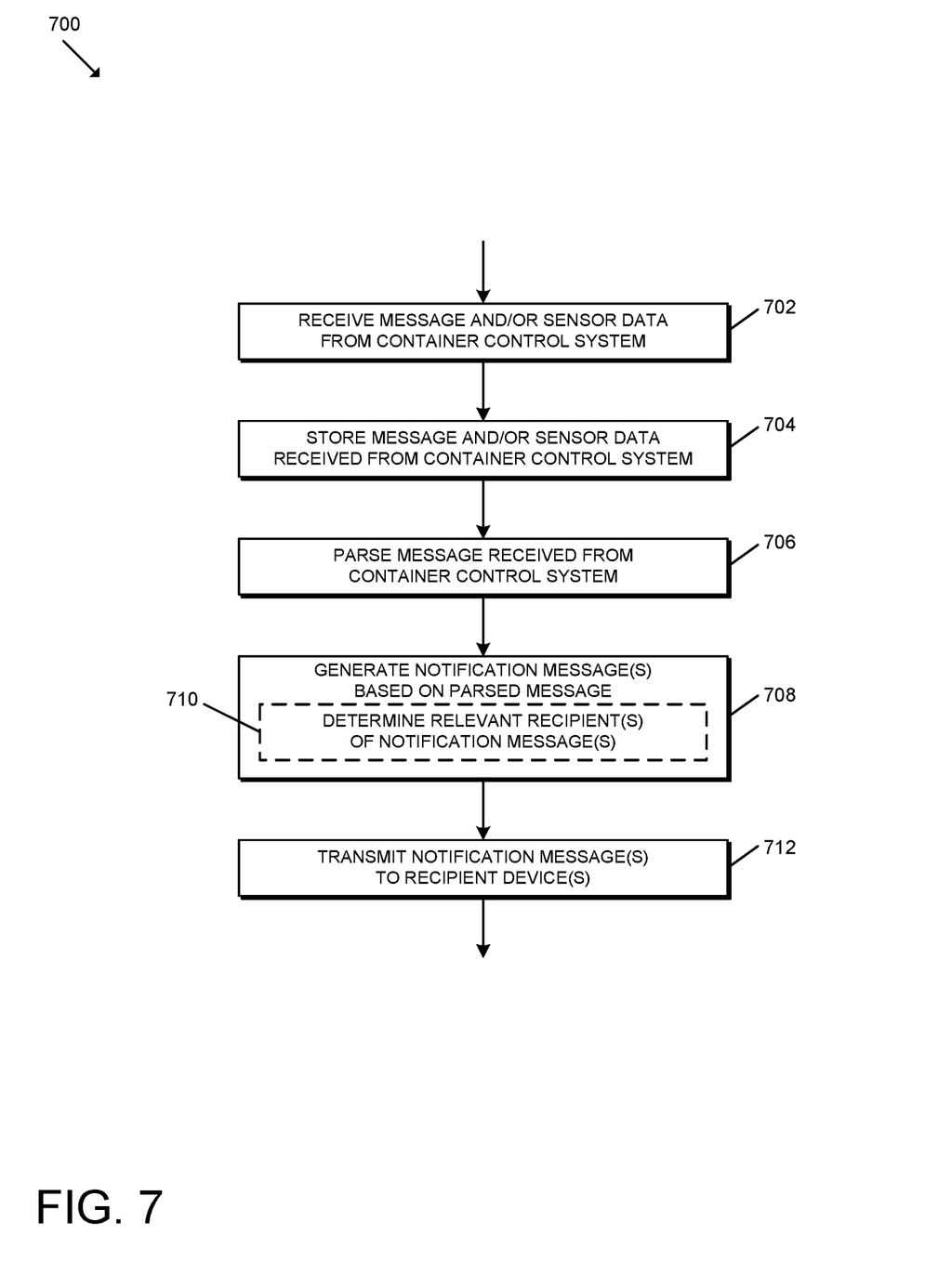
FIG. 7 is a simplified flow diagram of at least one embodiment of a method for notifying recipient devices of the status of vaccines within an insulated portable container including the container control system of FIG. 1.

Referring now to FIG. 7, in use, the vaccine monitoring system 100 or, more specifically, the cloud server 106 may execute a method 700 for notifying recipient devices of the status of vaccines within an insulated portable container (e.g., the insulated portable container 400 of FIG. 4). It should be appreciated that the particular blocks of the method 700 are illustrated by way of example, and such blocks may be combined or divided, added or removed, and/or reordered in whole or in part depending on the particular embodiment, unless stated to the contrary. The illustrative method 700 begins with block 702 in which the cloud server 106 receives a message, sensor data, and/or other relevant data/information from the container control system 102 (see block 516 of FIG. 5). In block 704, the cloud server 106 stores the message, sensor data, and/or other relevant data/information received from the container control system 102 to the memory of the cloud server 106 (e.g., in a database or other suitable data structure).

In block 706, the cloud server 106 parses the message received from the container control system 102 and, in block 708, the cloud server 106 generates one or more notification messages based on the parsed message. In doing so, in block 710, the cloud server 106 may determine the relevant recipient(s) of the notification message(s). In block 712, the cloud server 106 transmits the notification message(s) to the corresponding recipient device(s). For example, in some embodiments, the cloud server 106 may receive a message from the container control system 102 that is indicative of the temperature of the vaccines in the corresponding insulated portable container and, in turn, the cloud server 106 may transmit a corresponding notification message to the mobile device 108 of the vaccination field team. In some embodiments, the notification message is transmitted to the mobile device 108 of the vaccination field team as an SMS message, for example, as more sophisticated mobile devices and/or networks may be unavailable in many regions. However, in other embodiments, the container control system 102 transmit the message via another communication medium (e.g., email, pre-recorded or automated audio message, etc.). As such, it should be appreciated that the container control system 102 may utilize a set of notification rules, parameters, and/or configurations in determining the particular recipient devices and/or the communication medium.

Although the blocks 702-712 are described in a relatively serial manner, it should be appreciated that various blocks of the method 700 may be performed in parallel in some embodiments.

What is claimed is:

1. A vaccine monitoring system, comprising:
a server comprising a first processor and a first memory having a first plurality of instructions stored thereon; and
an insulated portable container for transporting a tetanus-containing vaccine in a temperature-stable environment, the insulated portable container structured to be less than four cubic feet in size and comprising:
a housing having a first chamber defined therein that stores the tetanus-containing vaccine during transport of the tetanus-containing vaccine;
a buffered temperature sensor container defining a second chamber that houses a buffering agent;
a temperature sensor positioned within the buffering agent that generates sensor data representative of a temperature of the tetanus-containing vaccine; and
a microcontroller secured to the housing within the first chamber, electrically coupled to the temperature sensor, and including a cellular communication circuitry, a second processor, and a second memory comprising a second plurality of instructions stored thereon that, in response to execution by the second processor, causes the microcontroller to (i) receive the sensor data from the temperature sensor, (ii) determine whether the sensor data is associated with a notification range, (iii) establish a cellular communication connection with the server using the cellular communication circuitry in response to a determination that the sensor data is associated with the notification range, and (iv) transmit, via the established cellular communication connection, a message to the server indicating that the sensor data is associated with the notification range; and wherein, in response to execution of the first plurality of instructions by the first processor, the server is configured to (i) parse the message received from the insulated portable container, (ii) generate a notification message indicative of the temperature of the tetanus-containing vaccine based on the parsed message, and (iii) transmit the notification message to a mobile device of a vaccination field team.

2. The vaccine monitoring system of claim 1, wherein to determine whether the sensor data is associated with the notification range comprises to analyze the sensor data to estimate whether the temperature of the tetanus-containing vaccine is at a temperature within the notification range; and
wherein the notification range is a range of temperatures of the tetanus-containing vaccine at which the microcontroller is to transmit a warning message to the server.

3. The vaccine monitoring system of claim 1, wherein the microcontroller further includes a global positioning system (GPS) circuitry;

wherein the second plurality of instructions further causes the microcontroller to (i) receive additional sensor data from the GPS circuitry and (ii) determine a location of the insulated portable container based on the additional sensor data of the GPS circuitry; and wherein to transmit the message to the server comprises to transmit at least one of the location or the additional sensor data to the server.

4. The vaccine monitoring system of claim 3, wherein to determine whether the sensor data is associated with the notification range comprises to analyze the sensor data to estimate whether a rate of change of the temperature of the tetanus-containing vaccine exceeds a maximum rate of change that allows the insulated portable container to arrive at a target destination without exceeding a temperature limit of the tetanus-containing vaccine based on the determined location of the insulated portable container and a rate of travel of the insulated portable container.

5. The vaccine monitoring system of claim 3, wherein to determine whether the sensor data is associated with the notification range comprises to:

determine a distance between the location of the insulated portable container and a target destination of the insulated portable container based on the additional sensor data from the GPS circuitry;

determine a maximum rate of change of the temperature of the tetanus-containing vaccine that allows the insulated portable container to travel the distance without exceeding a temperature limit of the tetanus-containing vaccine; and determine whether a current rate of change of the temperature of the tetanus-containing vaccine exceeds the maximum rate of change.

6. The vaccine monitoring system of claim 1, wherein the second plurality of instructions further causes the microcontroller to:

determine whether an update period has expired subsequent to successful transmission of prior sensor data based on a timer of the microcontroller;

establish the cellular communication connection with the server in response to a determination that the update period has expired; and transmit, via the established cellular communication connection, a second message to the server indicative of the temperature of the tetanus-containing vaccine.

7. The vaccine monitoring system of claim 1, wherein to determine that the sensor data is associated with the notification range comprises to determine that the sensor data indicates that the temperature of the tetanus-containing vaccine is less than two degrees Celsius or greater than eight degrees Celsius.

8. The vaccine monitoring system of claim 1, wherein the second plurality of instructions further causes the microcontroller to validate the sensor data prior to transmission of the message to the server via the established cellular communication connection.

9. The vaccine monitoring system of claim 8, wherein to validate the sensor data prior to the transmission of the message to the server via the established cellular communication connection comprises to:

determine that the temperature of the tetanus-containing vaccine represented by the sensor data is within an expected temperature range;

determine that no hardware error has occurred; and determine that the sensor data is in a proper data format.

10. The vaccine monitoring system of claim 1, wherein the mobile device is different and separate from the insulated portable container; and wherein to transmit the notification message to the mobile device of a vaccination field team comprises to transmit an SMS message to the mobile device.

11. The vaccine monitoring system of claim 1, wherein the second plurality of instructions further causes the microcontroller to disconnect the established cellular communication connection with the server and place the cellular communication circuitry in a sleep state in response to transmission of the message to the server.

12. The vaccine monitoring system of claim 1, wherein the microcontroller is positioned within a microcontroller housing secured to the housing of the insulated portable container within the first chamber;

wherein the second chamber of the buffered temperature sensor container houses the temperature sensor within the buffering agent; and wherein the temperature sensor is coupled to the microcontroller via an electrical coupling between the temperature sensor within the buffered temperature sensor container and the microcontroller within the microcontroller housing.

13. The vaccine monitoring system of claim 12, wherein the microcontroller housing is secured to an insulation layer of the housing of the insulated portable container within the first chamber.

14. An insulated portable container capable of manually transporting vaccines in a temperature-stable environment by a single person, the insulated portable container comprising:

a housing having one or more hard shell walls, an insulation layer secured to an interior side of the one or more hard shell walls, and a first chamber defined by the insulation layer that stores one or more vaccines during transport;

a microcontroller housing secured to the insulation layer of the housing;

a buffered temperature sensor container having a second chamber defined therein that houses a buffering agent;

a temperature sensor positioned within the buffering agent in the second chamber that generates sensor data representative of a temperature of the one or more vaccines; and a control system positioned within the microcontroller housing electrically coupled to the temperature sensor via an electrical coupling between the microcontroller housing and the buffered temperature sensor container, and including a processor and a memory comprising a plurality of instructions stored thereon that, in response to execution by the processor, causes the control system to:

receive the sensor data from the temperature sensor;

determine whether the sensor data is associated with a notification range;

establish a long-range wireless communication connection with a server in response to a determination that the sensor data is associated with the notification range; and transmit, via the established long-range wireless communication connection, a message to the server indicating that the sensor data is associated with the notification range.

15. The insulated portable container of claim 14, wherein to determine whether the sensor data is associated with the notification range comprises to analyze the sensor data to estimate whether the temperature of the one or more vaccines is at a temperature within the notification range; and wherein the notification range is a range of temperatures of the one or more vaccines at which the control system is to transmit a warning message to the server.

16. The insulated portable container of claim 14, wherein to determine whether the sensor data is associated with the notification range comprises to analyze the sensor data to estimate whether a rate of change of the temperature of the one or more vaccines exceeds an expected rate of change.

17. The insulated portable container of claim 14, further comprising a location sensor;

wherein the plurality of instructions further causes the control system to (i) receive additional sensor data from the location sensor and (ii) determine a location of the insulated portable container based on the additional sensor data of the location sensor; and wherein to transmit the message to the server comprises to transmit at least one of the location or the additional sensor data to the server.

18. The insulated portable container of claim 17, wherein to determine whether the sensor data is associated with the notification range comprises to analyze the sensor data to estimate whether a rate of change of the temperature of the one or more vaccines exceeds a maximum rate of change that allows the insulated portable container to arrive at a target destination without exceeding a temperature limit of the one or more vaccines based on the determined location of the insulated portable container.

19. The insulated portable container of claim 14, wherein the plurality of instructions further causes the control system to:

determine whether an update period has expired subsequent to successful transmission of prior sensor data based on a timer of the control system;

establish the long-range wireless communication connection with the server in response to a determination that the update period has expired; and transmit, via the established long-range wireless communication connection, a second message to the server indicative of the temperature of the one or more vaccines.

20. The insulated portable container of claim 14, wherein each of the one or more vaccines is a tetanus-containing vaccine; and wherein to determine that the sensor data is associated with the notification range comprises to determine that the sensor data indicates that the temperature of the one or more vaccines is less than two degrees Celsius or greater than eight degrees Celsius.

* * * * *